United States Patent
Apajalahti et al.

(10) Patent No.: US 6,638,746 B2
(45) Date of Patent: Oct. 28, 2003

(54) PHYTASE FROM BACILLUS SUBTILIS, GENE ENCODING SAID PHYTASE, METHOD FOR ITS PRODUCTION AND USE

(75) Inventors: Juha Apajalahti, Kantvik (FI); Pekka Heikkinen, Kantvik (FI); Janne Kerovuo, Kantvik (FI); Marko Lauraeus, Kantvik (FI); Andrew Morgan, Marlborough (GB); Paivi Nurminen, Kantvik (FI); Osmo Siikanen, Kantvik (FI)

(73) Assignee: Finnfeeds International Ltd., Marlborough (GB)

( * ) Notice: Subject to any disclaimer, the term of this patent is extended or adjusted under 35 U.S.C. 154(b) by 0 days.

(21) Appl. No.: 10/251,503

(22) Filed: Sep. 20, 2002

(65) Prior Publication Data

US 2003/0157680 A1 Aug. 21, 2003

Related U.S. Application Data

(63) Continuation of application No. 09/242,499, filed on Jan. 10, 2000, now abandoned.

(51) Int. Cl.⁷ .................................................. C12N 9/16

(52) U.S. Cl. ...................................................... 435/196

(58) Field of Search ............................... 435/69.1, 196, 435/252.1, 252.33, 320.1; 536/23.2, 23.7

(56) References Cited

U.S. PATENT DOCUMENTS 5,863,533 A * 1/1999 Van Gorcom et al. ..... 424/94.6

* cited by examiner

*Primary Examiner*—Ponnathapu Achutamurthy
*Assistant Examiner*—Christian L. Fronda
(74) *Attorney, Agent, or Firm*—Fitch, Even, Tabin & Flannery

(57) ABSTRACT

The present invention relates to phytase, nucleic acids encoding phytase as well as methods for the production of phytase and its use.

11 Claims, 10 Drawing Sheets

PHYTASE FROM BACILLUS SUBTILIS, GENE ENCODING SAID PHYTASE, METHOD FOR ITS PRODUCTION AND USE

This is a continuation, of prior application Ser. No. 09/242,499, filed Jan. 10, 2000 now abondonded, which is hereby incorporated herein by reference in its entirety.

The present invention relates to phytase, nucleic acids encoding phytase as well as methods for the production of phytase and its use.

BACKGROUND OF THE INVENTION

Phosphorous is an essential element for growth. A substantial amount of the phosphorous found in many foods and animal feeds is present in the form of phosphate which is covalently bound in a molecule known as phytate (myo-inositol hexakisphosphate). Since phytate itself is poorly digested and phosphate is to a large extent absorbed in the small intestine of an animal, phosphate sequestered in phytate and not made available to an animal in the small intestine is not absorbed, passes through the digestive tract and is excreted. This leads to an increased ecological phosphorus burden to land and water. In addition, since phytate chelates several essential minerals and prevents or inhibits their absorption in the digestive tract, phytate decreases the nutritional value of food and animal feeds.

Another problem associated with poor phytate digestability is that inorganic phosphates need to be added to animal feeds, thereby increasing their costs.

Phytate is converted by enzymes known as phytases which catalyse the hydrolysis of phytate to inositol and inorganic phosphate. Phytase is found in wheat bran and plant seeds and is known to be produced by various microorganisms including yeast, fungi and bacteria.

Among known fungal phytases, *Aspergillus terreus* phytase was purified to homogeneity by Yamada et al. (Agr. Biol. Chem., 32 (10) (1968), 1275–1282) and shown to have a pH optimum of pH 4.5, a temperature optimum of about 70° C. at pH 4.5 and a thermal stability over a temperature range from 30 to 60° C. at pH 4.5. However, said enzyme was shown to be completely inactive at neutral pH values, particularly at pH 7.0.

In addition, the *Aspergillus ficuum* phytase isolated and characterised by H. J. Ullah and D. M. Gibson (Preparative Biochemistry, 17 (1) (1987), 63–91) was shown to have two pH optima, one at 2.2 and the other at 5.0–5.5, a temperature optimum of 58° C. at pH 5.0 and a thermal stability up to 68° C. at pH 5.0. However, as is the case with *Aspergillus terreus* phytase, *Aspergillus ficuum* phytase was shown to be inactive at pH 7.0.

DNA sequences encoding phytases from *Aspergillus terreus* (EP 684 313) and *Aspergillus ficuum* (EP 420 358) as well as *Aspergillus niger* var. *awamori* (Piddington et al., (1993) Gene, 133, 55–62) have been characterised and recombinantly expressed.

Phytases are also known from bacterial sources such as *Bacillus subtilis* (V. K. Powar and V. Jagannathan, (1982) J. Bacteriology, 151 (3), 1102–1108) and *Bacillus subtilis* (natto) (M. Shimizu, (1992) Biosci. Biotech. Biochem., 56 (8), 1266–1269 and Japanese Patent Application 6-38745).

*Bacillus subtilis* (natto) phytase described by Shimizu (supra) was purified to homogeneity by SDS-PAGE and was shown to have a molecular weight of between 36 and 38 kD. This enzyme was shown to have a pH optimum between pH 6.0 and 6.5 when measured in an assay solution at 37° C. comprising 0.1 M maleic acid, 2 mM $CaCl_2$ and 1.6 mM sodium phytate and a pH optimum of pH 7.0 when assayed in a solution comprising 0.1 M Tris-HCl buffer, 2 mM $CaCl_2$ and 1.6 mM sodium phytate at 37° C. The temperature optimum for this phytase was shown to be 60° C. and the enzyme is stable up to 50° C. when incubated in the above mentioned assay solution containing Tris-HCl buffer for 15 min. The specific activity of this purified *Bacillus subtilis* (natto) phytase in said Tris-HCl containing solution was reported as 8.7 U/mg protein. One unit of phytase was defined as the amount of enzyme required to liberate one μmol of Pi per minute under tha assay conditions. This definition is used throughout.

Powar et al. (supra) described the isolation of a phytate specific phosphatase preparation from *Bacillus subtilis* which has a molecular weight of 36.5 kD. This enzyme preparation, which was purified by SDS-PAGE and found to comprise two phytase isozymes, was shown to have a pH optimum between 7.0 and 7.5 when measured in an assay solution comprising 0.1 M Tris-HCl buffer, 0.5 mM $CaCl_2$ and 0.34 mM sodium phytate at 30° C. This phytase isozyme mixture exhibited a maximum activity at a temperature of 60° C. and was stable up to a temperature of 70° C. The specific activity of the purified enzyme was reported as 8.5 to 9.0 U/mg protein when measured in the above assay solution. In addition, it was reported by Powar et al (supra) that the purified isozyme mixture contained proteolytic activity which resulted in the loss of activity.

The amino acid sequence of Bacillus phytase as well as nucleic acids which encode Bacillus phytases are not known to date.

The idea of supplementing foods and animal feed with naturally occurring or recombinant phytases in order to enzymatically convert phytate to digestible phosphate during food and animal feed processing has been described. JP-A-6-38745 describes the use of purified naturally occurring *Bacillus subtilis* (natto) phytase for use in processing feeds and foods. In addition, EP 420 358 and EP 684 313 describe the use of Aspergillus phytase in animal feeds.

Furthermore, it has also been suggested to add phytase to animal feeds which have already been processed in order to allow the enzymatic action of said phytases to take place in the digestive tract of the animal.

However, the above mentioned Aspergillus phytases are either inactive or lose a substantial amount of their activity at the temperature and/or pH at which foods or animal feeds are processed (generally 65 to 95° C., pH 5.5 to 7.5) and at the pH of the small intestine of monogastric animals (generally 37–41° C., pH 5.5 to 7.5).

Furthermore, the specific activity, and therefore the relative activity, of the above mentioned Bacillus phytases is very low under the above conditions.

SUMMARY OF THE INVENTION

Due to the difference in the temperatures and/or pH used during processing of foodstuffs and in the digestive tract of animals, it is desirable to have available a phytase which has a high specific activity as well as a high relative activity both at the processing temperature and/or pH of foods and animal feeds and at the temperature and/or pH in the digestive tract of animals in order to both maximise the effects of phytase during food and feed processing, during digestion within the digestive tract and to reduce the phosphorous burden to the environment resulting from digestion of phytate containing animal feedstuffs.

Moreover, a method for the production of large quantities of phytase which fulfils the above criteria is also desirable for the economic production of said foods and animal feeds.

An object of the present invention is to provide phytase with a high specific activity which is capable of functioning with a high relative activity during the processing of foods and animal feeds and/or is capable of functioning with high relative activity in the digestive tract of farmed animals.

A further object of the present invention is to provide nucleic acid molecules which encode phytase of the present invention.

A further object of the present invention is to provide methods for the production of said phytase as well as means for delivering said phytase to said animals.

Other objects of the present invention will become apparent from the following detailed specification.

Subject matter of the invention is phytase or a functional derivative thereof, characterised in that said phytase has a specific activity of at least 20 U/mg protein, wherein said specific activity is determined by incubating said phytase in a solution containing 100 mM Tris-HCl, pH 7.5, 1 mM $CaCl_2$, and 1.6 mM sodium phytate at 37° C. for 30 minutes. Preferably, the phytase of the present invention has a specific activity of at least 29 U/mg protein, more preferably at least 80 U/mg protein, and most preferably at least 88 U/mg protein when assayed under the above conditions.

According to a preferred embodiment, said phytase has a pH optimum of at least pH 6.5, wherein said pH optimum is determined by incubating said phytase in a solution containing 100 mM maleic acid-Tris, 1 mM $CaCl_2$, and 1.6 mM sodium phytate at 37° C. for 30 minutes or a pH optimum of at least pH 7.0, wherein said pH optimum is determined by incubating said phytase in a solution containing 100 mM Tris-HCl, 1 mM $CaCl_2$, and 1.6 mM sodium phytate at 37° C. for 30 minutes or by incubating said phytase in a solution containing wheat bran extract, 1 mM $CaCl_2$, and 1.6 mM sodium phytate at 37° C. for 30 minutes.

It is advantageous for phytase to have a relatively high activity both during food or feed processing and in the digestive tract of farmed animals such that the enzyme is capable of functioning well under both conditions. The activity of phytase of the present invention in feed or food during processing is preferably greater than or equal to 30%, more preferably greater than or equal to 35%, and most preferably greater than or equal to 37%, compared to the activity of said phytase in the digestive tract, preferably the crop and/or small intestine, of a farm animal.

In addition, said phytase is preferably capable of functioning in the presence of digestive enzymes found in the small intestine of animals. Enzymes which are found in the small intestine of animals include pancreatic enzymes such as trypsin, chymotrypsin and lipase.

The present invention relates to phytase with one or more of the above characteristics.

The phytase of the present invention is obtainable from a microbial source, preferably a strain of Bacillus, more preferably a Bacillus strain selected from the group comprising *Bacillus subtilis* and *Bacillus amyloliquefaciens*, and most preferably *Bacillus subtilis* strain B 13 deposited on Aug. 1, 1996 at the National Collections of Industrial and Marine Bacteria, Ltd. (NCIMB) in Scotland under accession number NCIMB-40819.

In a preferred embodiment, phytase of the present invention comprises the amino acid sequence according to SEQ ID NO: 1 or a functional derivative thereof. The term "a functional derivative thereof" as it relates to phytase is used throughout the specification to indicate a derivative of phytase which has the functional characteristics of phytase of the present invention. Functional derivatives of phytase encompass naturally occurring, synthetically or recombinantly produced peptides or peptide fragments, mutants or variants which may have one or more amino acid deletions, substitutions or additions which have the general characteristics of the phytase of the present invention.

Further subject matter of the present invention is an isolated nucleic acid or a functional derivative thereof, which encodes a phytase having one or more of the above characteristics. Preferably, said nucleic acid comprises a DNA sequence according to SEQ ID NO: 1 or a functional derivative thereof, or hybridises to a DNA sequence according to SEQ ID NO: 1 or a functional derivative thereof.

Further subject matter is an isolated nucleic acid which encodes a phytase or a functional derivative thereof, characterized in that said nucleic acid hybridises to a DNA according to SEQ ID NO: 1 and encodes a phytase having a pH optimum of greater than or equal to pH 5.0 and a specific activity of at least 10 U/mg protein as determined in a solution containing 100 mM maleic acid-Tris, 1 mM $CaCl_2$, and 1.6 mM sodium phytate at 37° C. for 30 minutes.

Said nucleic acid is preferably a DNA molecule. The term "a functional derivative thereof" as it relates to nucleic acids encoding phytase is used throughout the specification to indicate a derivative of a nucleic acid which has the functional characteristics of a nucleic acid which encodes phytase. Functional derivatives of a nucleic acid which encode phytase of the present invention encompass naturally occurring, synthetically or recombinantly produced nucleic acids or fragments, mutants or variants thereof which may have one or more nucleic acid deletions, substitutions or additions and encode phytase characteristic of the present invention. Variants of nucleic acid encoding phytase according to the invention include alleles and variants based on the degeneracy of the genetic code known in the art. Mutants of nucleic acid encoding phytase according to the invention include mutants produced via site-directed mutagenesis techniques (see for example, Botstein, D. and Shortle, D., 1985, Science 229: 1193–1201 and Myers, R. M., Lerman, L. S., and Maniatis, T., 1985, Science 229: 242–247), error-prone PCR (see for example, Leung, D. W., Chen, E., and Goeddel, D. V., 1989, Technique 1: 11–15; Eckert, K. A. and Kunkel, T. A., 1991, PCR Methods Applic. 1: 17–24; and Cadwell, R. C. and Joyce, G. F., 1992, PCR Methods Applic. 2: 28–33) and/or chemical-induced mutagenesis techniques known in the art (see for example, Elander, R. P 'Microbial screening, Selection and Strain Improvement' in Basic Biotechnology, J. Bu'lock and B. Kristiansen Eds., Academic Press, New York, 1987, 217).

Subject matter of the present invention is also a method for the production of a nucleic acid of the invention, characterised in that a probe comprising a nucleic acid as described above is hybridised under standard conditions to a sample suspected of containing said nucleic acid and said nucleic acid is recovered. Standard techniques employing said probe for hybridisation include Southern blotting (see for example, Sambrook et al., Molecular Cloning, a Laboratory Manual, 2nd. Edition, Cold Spring Harbor Laboratory Press, 1989), PCR and RT-PCR(see for example, PCR Protocols: A Guide to Methods and Applications, Innis, M. A., Gelfand, D. H., Sninsky, J. J. and White, T. J. Eds., Academic Press New York, 1990). Standard conditions for hybridization are preferably 6×SSC, 0.5% SDS, 50° C. overnight or functional equivalents thereof for Southern blotting and for PCR: 5 mM $Mg^{2+}$, Taq enzyme, premelting, 94° C. for 2 min and 30 cycles of melting at 92° C. for 20 sec, annealing at 50° C. for 30 sec and extension at 72° C. for 1 min, or functional equivalents thereof.

Subject matter of the present invention is also a vector comprising a DNA molecule of the present invention. Preferably, said vector is characterised in that said DNA molecule is functionally linked to regulatory sequences capable of expressing phytase from said DNA sequence. Preferably, said DNA molecule comprises a leader sequence capable of providing for the secretion of said phytase. Said regulatory sequences can comprise prokaryotic or eukaryotic regulatory sequences.

Depending on whether the phytase of the invention is expressed intracellularly or is secreted, a DNA sequence or vector of the invention can be engineered such that the mature form of the phytase of the invention is expressed with or without a natural phytase signal sequence or a signal sequence which functions in Bacillus, other prokaryotes or eukaryotes. Expression can also be achieved by either removing or partially removing said signal sequence.

Subject matter of the present invention is also a prokaryotic host cell transformed by a nucleic acid or vector as described above. Preferably said host cell is selected from the group comprising E. coli, Bacillus sp., Lactobacillus and Lactococcus.

Subject matter of the present invention is also a eukaryotic host cell transformed by a nucleic acid or vector as described above. Preferably said host cell is selected from the group comprising Aspergillus sp., Humicola sp., Pichia sp., Trichoderma sp. Saccharomyces sp. and plants such as soybean, maize and rapeseed.

Subject matter of the present invention is also a method for the recombinant production of phytase, characterised in that a prokaryotic or eukaryotic host cell as described above is cultured under suitable conditions and said phytase is recovered.

A preferred embodiment of the phytase of the present invention is a phytase obtainable according to the above method. Further subject matter of the present invention is the use of bacterial cells or spores capable of producing phytase according to the invention as a probiotic or direct fed microbial product. Preferred embodiments for said uses are phytase-producing Bacillus sp. and Lactobacillus sp. of the invention.

Further subject matter of the invention is also a use of phytase according to the present invention in food or animal feed.

Further subject matter is food or animal feed comprising phytase according to the invention. Preferably, said food or animal feed comprises phytase as an additive which is active in the digestive tract, preferably the crop and/or small intestine, of said animal, wherein said animal is preferably selected from the group comprising avians including poultry, ruminants including bovine and sheep, pig, and aquatic farm animals including fish and shrimp. Said additive is also preferably active in food or feed processing.

Further subject matter is food or animal feed comprising prokaryotic cells or spores capable of expressing phytase according to the present invention.

Subject matter of the present invention is also a method for the production of a food or animal feed, characterised in that phytase according to the invention is mixed with said food or animal feed. Said phytase is added as a dry product before processing or as a liquid before or after processing. If a dry powder is used, the enzyme would be diluted as a liquid onto a dry carrier such as milled grain.

Subject matter of the present invention is also a method for the production of a food or animal feed, characterised in that prokaryotic cells and/or spores capable of expressing phytase according to the invention are added to said food or animal feed.

Subject matter of the present invention is also a use of phytase according to the invention with or without accessory phosphatases in the production of inositol and inorganic phosphate.

Further subject matter of the present invention is a method for the reduction of levels of phosphorous in animal manure, characterised in that an animal is fed an animal feed according to the invention in an amount effective in converting phytate contained in said animal feed.

Definitions

The term "phytase" is defined throughout the specification as a protein or polypeptide which is capable of catalysing the hydrolysis of phytate and releasing inorganic phosphate.

Specific activity of phytase is defined throughout specification as the number of units (U)/mg protein of a solution comprising phytase, wherein said phytase is detectable as a single band by SDS-PAGE. One unit is the amount of enzyme required to liberate one $\mu$mol of Pi per minute when said enzyme is incubated in a solution containing 100 mM Tris-HCl, pH 7.5, 1 mM $CaCl_2$, and 1.6 mM sodium phytate at 37° C. for 30 minutes.

Relative activity of phytase is defined throughout the specification as the activity of the enzyme at a given temperature and/or pH compared to the activity of the enzyme at the optimal temperature and/or pH of said enzyme.

DETAILED DESCRIPTION OF THE INVENTION

Figure 1:
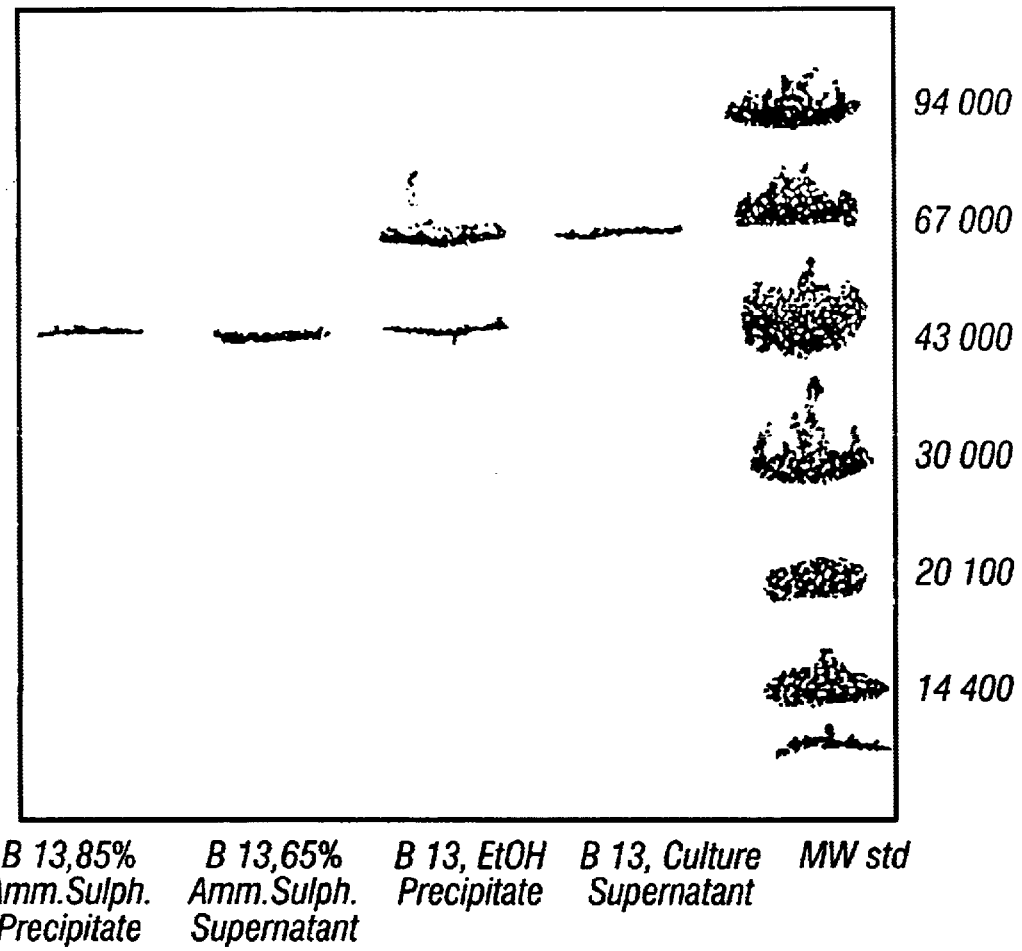
FIG. 1: SDS-PAGE gel of phytase purification (procedure)

The invention is more closely illustrated by the following examples.

EXAMPLE 1

Bacillus subtilis B 13 deposited at the National Collections of Industrial and Marine Bacteria, Ltd. (NCIMB) in Scotland under accession number NCIMB-40819 was used throughout the study.

Media

Luria medium, containing 5 g of yeast extract, 10 g of tryptone and 10 g of NaCl per liter, was used to grow the inoculum for the production of phytase.

Wheat bran extract was used as the enzyme production medium and it was prepared as follows. 100 grams of wheat bran was extracted with 1000 ml of water by autoclaving at 121° C. for 60 minutes. The extract was filtered through six layers of cheesecloth and then the volume of the extract was adjusted to one liter by addition of water. This extract was supplemented with: $(NH_4)_2SO_4$ 0.4 g, $MgSO_4 \cdot 7H_2O$ 0.2 g, casitone 10 g, $KH_2PO_4$ 0.5 g and $K_2HPO_4$ 0.4 g. The final pH of the extract was 6.5. The extract base was autoclaved at 121° C. for 15 minutes. Prio to inoculation, 5% $CaCl_2$ (filter sterilised) was added to the final concentration of 0.2%.

Production of Enzyme

Inoculum was grown up from the frozen stock in Luria medium supplemented with 0.2% $CaCl_2$. The initial inoculum was grown for 24 hours at 30° C. in a rotatory shaker. The cultivation was scaled up using successive 10% inoculations in wheat bran medium. For enzyme production the 5 liter batch was grown in wheat bran medium at 30° C. for 91 hours with vigorous shaking.

Protein Assay

Protein concentrations were determined by Bio-Rad Protein Microassay Procedure according to the recommendations of the manufacturer by using Bovine Serum Albumin as a standard.

Purification of Phytase

All purification steps were carried out at 0–4° C. unless otherwise stated. Bacteria were pelleted by centrifugation at 7000×g for 30 minutes. The volume of the collected supernatant was determined and $CaCl_2$ added to a final concentration of 1 mM. The enzyme was precipitated by adding three volumes of cold (−20° C.) ethanol, which was added with constant stirring to the supernatant. Stirring was continued for 45 minutes and the precipitation was carried out overnight. The precipitate was collected by centrifugation at 1800×g for 20 minutes. The collected precipitate was washed once with cold (−20° C.) ethanol and once with cold (−20° C.) acetone. Excess acetone was evaporated from the precipitate under nitrogen gas flow and then the drying was completed by lyophilisation.

The dried precipitate was dissolved in 300 ml of 100 mM Tris-HCl, pH 7.5, supplemented with 1 mM $CaCl_2$. Ammonium sulphate was added slowly to the solution under constant stirring until 65% saturation was reached. The solution was incubated at 4° C. overnight, cleared by centrifugation at 9000×g for 60 minutes at 4° C. and then ammonium sulphate added until 85% saturation was reached. The solution was again incubated over night at 4° C. Precipitate was collected by centrifugation as before and then dissolved in 100 mM Tris-HCl, pH 7.5, supplemented with 1 mM $CaCl_2$. Aliquots of enzyme preparation were stored at −20° C. When used for experiments the enzyme preparations were gel filtered to a desired defined buffer by using PD-10 (Pharmacia) gel filtration columns. The purification scheme of phytase is shown in Table 1.

TABLE 1

Specific activity of purified phytase

| Enzyme sample | volume (ml) | Protein conc. (mg/ml) | specific activity (U/mg) | total activity (U) | recovery (%) | purification factor |
|---|---|---|---|---|---|---|
| culture supernatant | 5000 | 0.3 | 8 | 10270 | 100 | 1.00 |
| rediss. EtOH precipitate | 305 | 2.1 | 15 | 9528 | 93 | 1.91 |

TABLE 1-continued

Specific activity of purified phytase

| Enzyme sample | volume (ml) | Protein conc. (mg/ml) | specific activity (U/mg) | total activity (U) | recovery (%) | purification factor |
|---|---|---|---|---|---|---|
| supernatant 65% $(NH_4)_2SO_4$ | 330 | 0.2 | 88 | 5720 | 56 | 11.19 |
| rediss. pellet 85% $(NH_4)_2SO_4$ | 20 | 3.8 | 29 | 2231 | 22 | 3.69 |

Estimation of Molecular Weight and Isoelectric Point

The molecular weight of phytase as purified above was estimated in Pharmacia Phast electrophoresis equipment by using SDS 8–25% gradient polyacrylamide gel electrophoresis (PhastGel® SDS-page) and the Pharmacia Low Molecular Weight Electrophoresis Calibration Kit as a standard according to recommendations by the manufacturer. The isoelectric point was determined with the same system using PhastGel IEF 3–9 isoelectric focusing gel and the Pharmacic IEF Calibration Kit as a standard.

Figure 2:
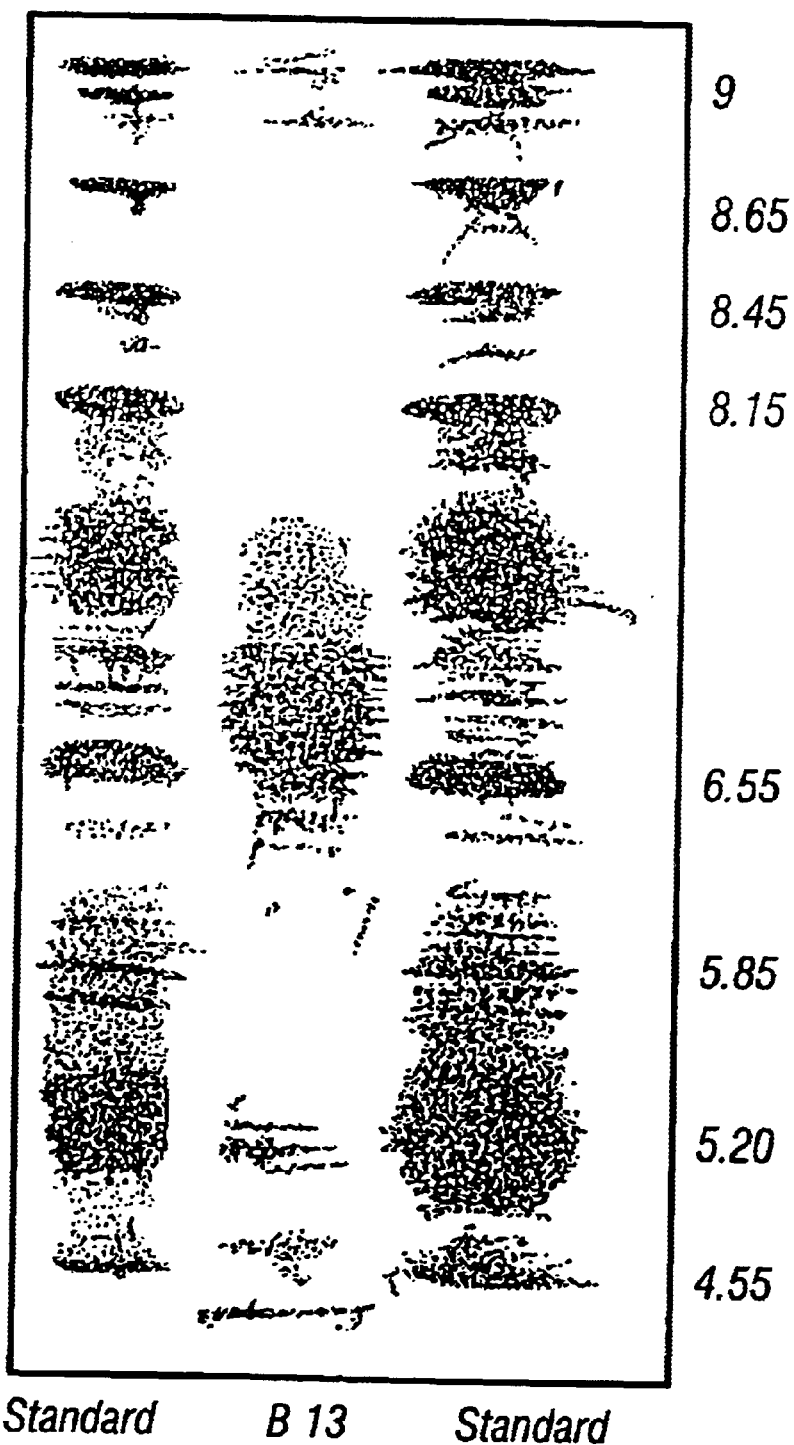
FIG. 2: Isoelectric focusing gel of purified phytase.
Figure 3A:
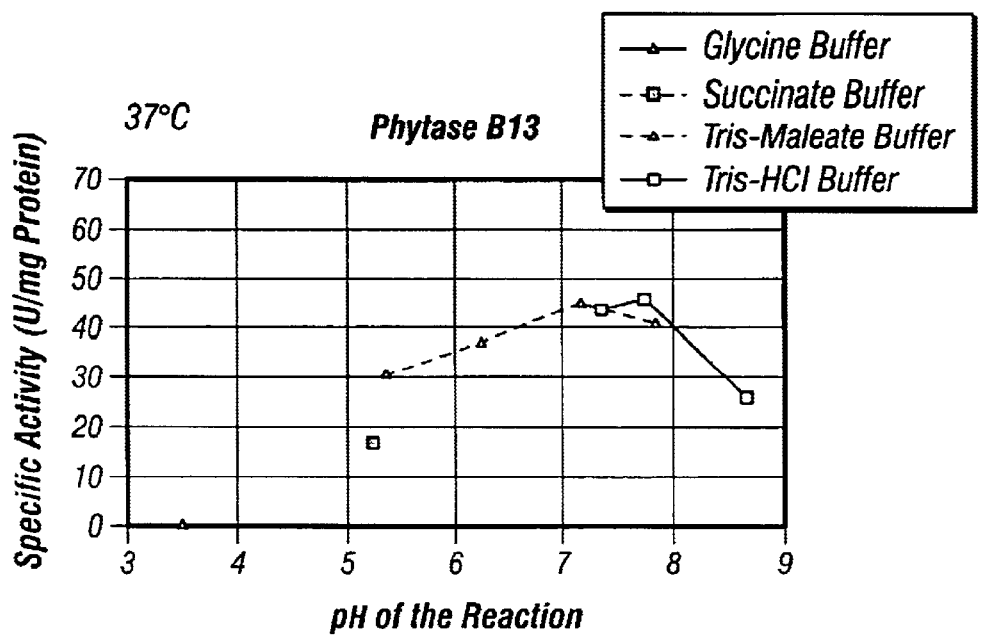
FIG. 3: Effect of pH on the activity of phytase at different temperatures.
Figure 3B:
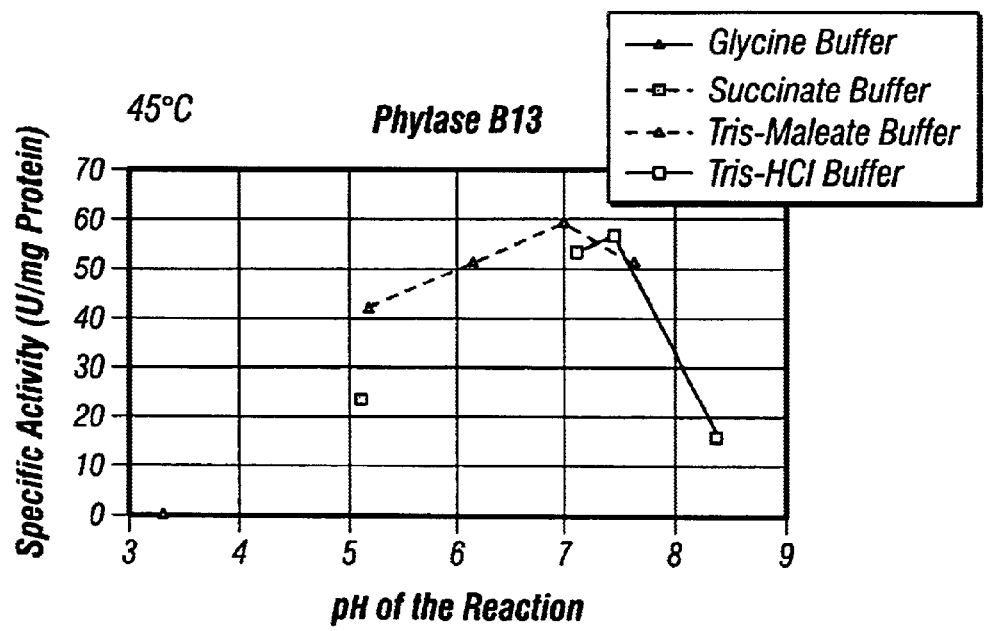
Figure 3C:
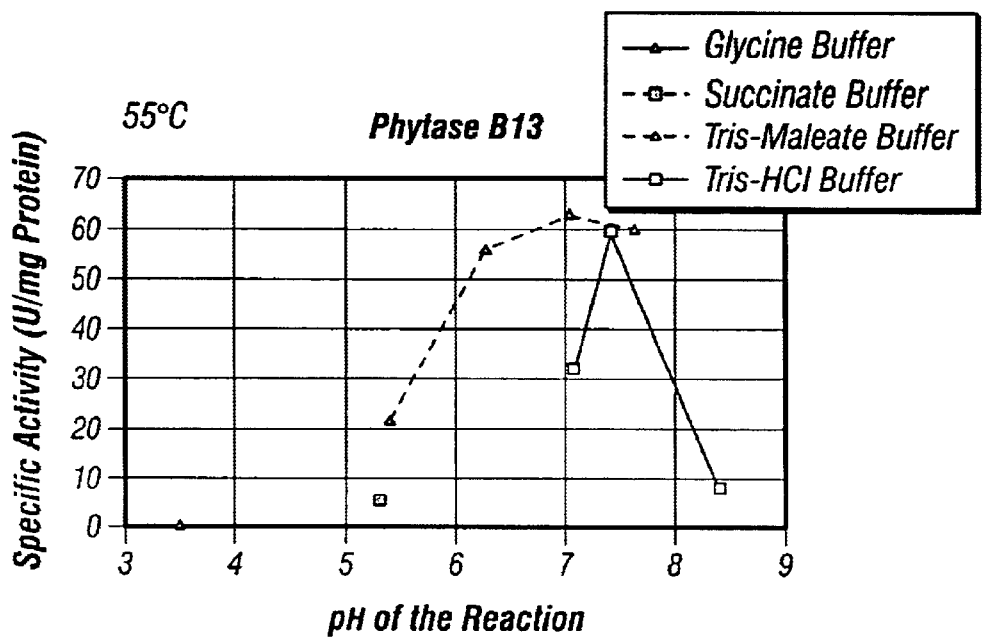
Figure 3D:
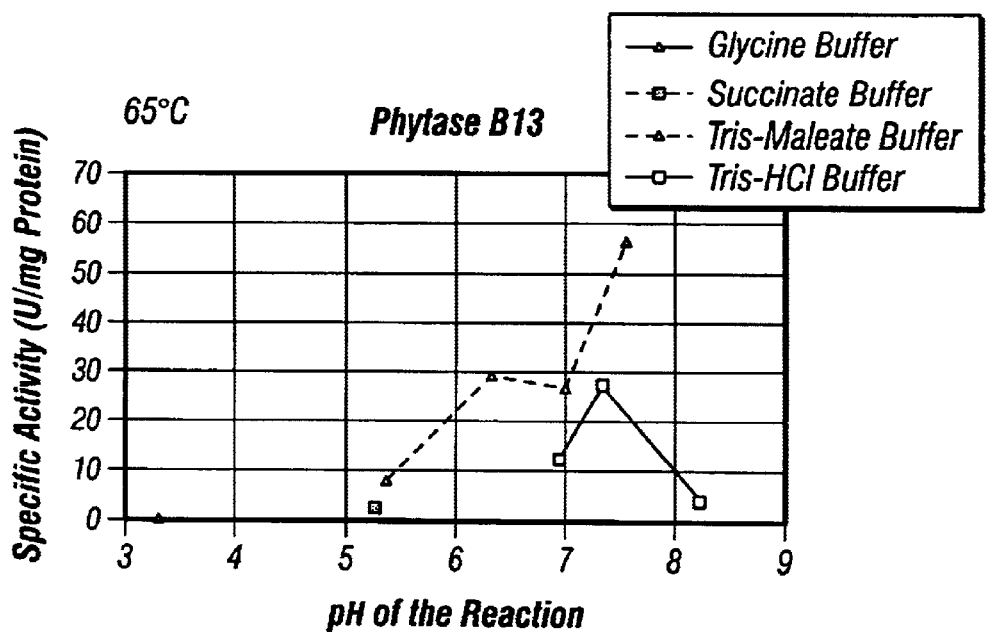
Figure 3E:
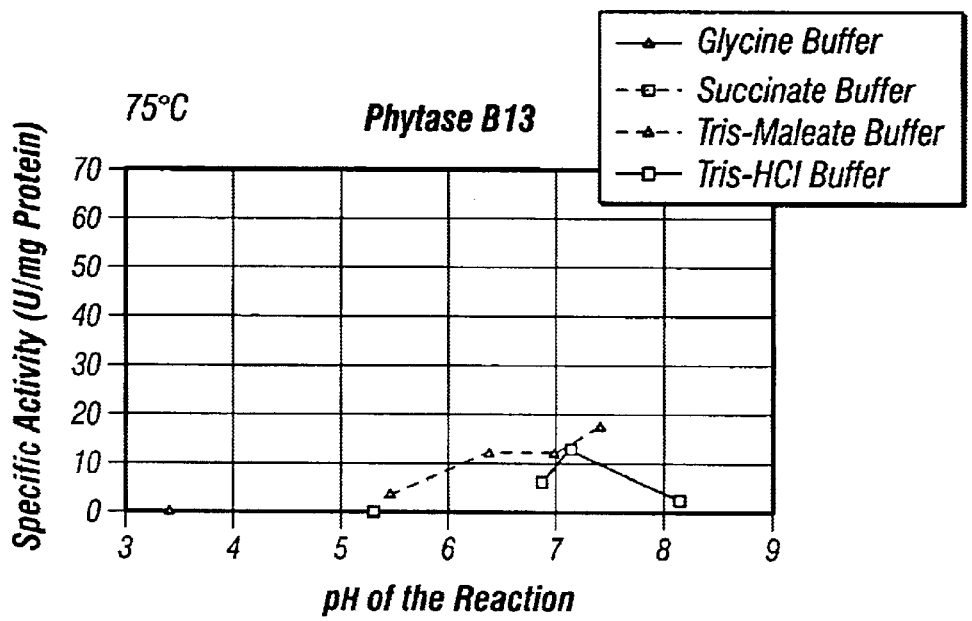

Molecular weight of the B 13 phytase was 43,000 as determined by SDS-PAGE (FIG. 1). Isoelectric pH of the B 13 phytase was 6.5 (FIG. 2).

Substrate Specificity

Substrate specificity of the phytase (in 0.1 M Tris-HCl, pH 7.5) was determined by using the standard activity assay of each enzyme. Besides phytic acid, β-glycerophosphate, D-glucose-6-phosphate, p-nitrophenylphosphate, ATP, ADP, AMP, fructose, 1,6-diphosphate, 3-phosphoglyceric acid, bis-(p-nitrophenyl)phosphate and α,β-methyleneadenosine-5′-diphosphate were used as alternative substrates. The results of the analysis of substrate specificity are shown in Table 2.

TABLE 2

Substrate specificity of phytase

| Substrate | Relative activity of phytase |
|---|---|
| phytic acid | 100 |
| β-glycerophosphate | 0 |
| D-glucose-6-phosphate | 0 |
| p-nitrophenylphosphate | 0 |
| ATP | 50 |
| ADP | 75 |
| AMP | 0 |
| fructose-1,6-phosphate | 0 |
| 3-phosphoglyceric acid | 0 |
| methyleneadenosine-5′-diphosphate | 0 |
| bis-(p-nitrophenyl)phosphate | 0 |

Enzyme Assay

Unless otherwise stated, the activity of phytase was measured by incubating 150 μl enzyme preparation with 600 μl of 2 mM sodium phytate in 100 mM Tris-HCl buffer pH 7.5, supplemented with 1 mM $CaCl_2$ for 30 minutes at 37° C. After incubation the reaction was stopped by adding 750 μl of 5% trichloroacetic acid. Phosphate released was measured against phosphate standard spectrophotometrically at 700 nm after adding 1500 μl of the colour reagent (4 volumes of 1.5% ammonium molybdate in 5.5% sulphuric acid and 1 volume of 2.7% ferrous sulphate; Shimizu, M., 1992; Biosci. Biotech. Biochem., 56:1266–1269). One unit of enzyme activity was defined as the amount of enzyme required to liberate one μmol Pi per min under assay conditions. The specific activity was expressed in units of enzyme activity per mg protein. The characteristics of the phytase purified in the above manner are summarised in Table 3.

TABLE 3

Characteristics of phytase

| Property | phytase |
|---|---|
| Molecular weight | 43,000 |
| Isoelectric point | 6.5 |
| Optimum pH at 37° C. | 7.5 |
| Optimum temperature | 55° C. (pH 7.1) | pH and Temperature Activity Profiles

Temperature and pH activity profiles of phytase were analysed in defined buffers and in wheat bran extract. The enzyme concentrations used in the assays gave linear orthophosphate release for the 30 minute incubation period under optimum conditions at 37° C.

Defined buffers used were 100 mM Glycine pH 3.0, 100 mM Succinate pH 5.0, 100 mM Tris-maleate pH 5.0, 6.0, 7.0 and 8.0, 100 mM Tris-HCl pH 7.5, 8 and 9. All buffers were supplemented with 2 mM sodium phytate and 1 mM $CaCl_2$. Enzyme assays were performed in these buffers at five different temperatures (37, 45, 55, 65 and 75° C.). 600 µl of a buffer was temperated at the relevant temperature and the enzyme reaction was started by adding 150 µl of an enzyme preparation. Reactions were stopped after 30 minutes incubation and liberated inorganic orthophosphate was measured as earlier described. Enzyme assays were run in duplicates. The true pH in the reaction mixture was measured in the beginning and at the end of each assay. Protein concentrations were measured as described earlier and the specific activities of enzymes were calculated at various pH and temperature.

Wheat bran extract was prepared by dissolving 50 g wheat bran in 500 ml of distilled water followed by autoclaving at 121° C. for 60 minutes. The extract was filtered through cheese cloth, volume adjusted to 500 ml with distilled water and then the extract was centrifuged at 15,000 rpm for 15 minutes and the supernatant collected. The aliquots of the supernatant were adjusted to pH 3.0, 5.5, 7.0, 8.0 and 9.0, diluted 1:10 in distilled water and supplemented with 2 mM sodium phytate and 1 mM $CaCl_2$. 600 µl of a pH adjusted wheat bran extract was temperated to desired temperature (37, 55 and 75° C.) and the enzyme reactions were started by adding 150 µl of enzyme preparation. Reactions were stopped after 30 minutes incubation and liberated inorganic orthophosphate was measured as described above. Enzyme assays were assayed in duplicates. The true pH of each reaction mixture was measured in the beginning and at the end of the enzyme assay.

Effect of pH on the Phytase Activity

Relative activity of phytase was determined over a pH ranging from 3.0 to 8.5 using both defined buffers and pH adjusted wheat bran extract. It was obvious that not only the pH of the buffer, but also acid composition of the buffer affected relative phytase activity. To cover the pH range, four different defined buffers or wheat bran extract, the pH of which was adjusted by HCl or NaOH addition, were used. Since enzyme addition affected pH of the reaction mixture, the true pH of each assay mixture was measured in the beginning and in the end of the 30 minute incubation. During the reaction the changes of pH were insignificant.

True reaction pH was used in the determination of pH activity profiles.

FIGS. 3a to 3e show the pH activity profiles of B 13 phytase in defined buffers at five different temperatures between 37 and 75° C. Irrespective of the reaction temperature, phytase showed highest phytase activity at pH 7.5.

Animal compound feed typically has a pH ranging from pH 5.5 to 7.5.

Figure 4:
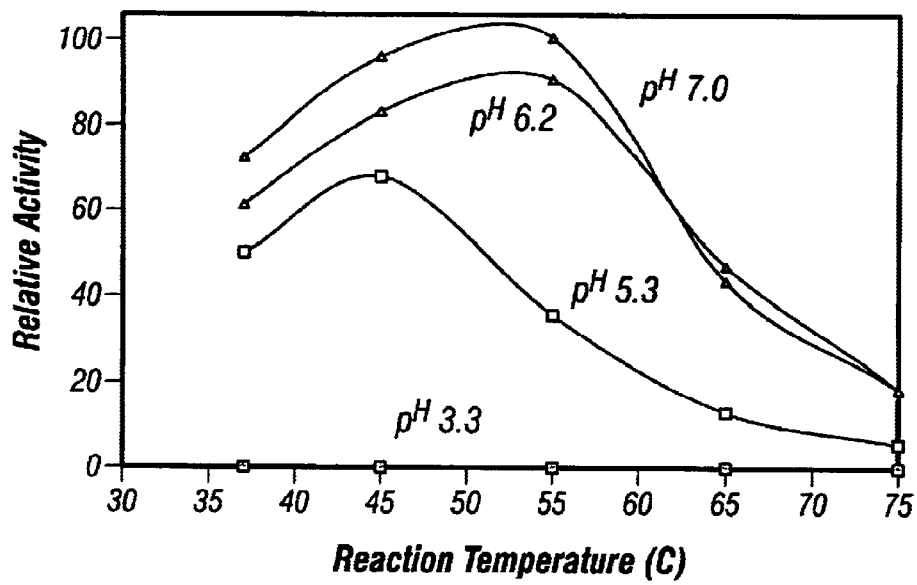
FIG. 4: Effect of pH on the temperature activity profile of phytase in defined buffers.

Temperature optimum of phytase was 55° C. The effect of pH on the temperature activity profile of phytase in the above defined buffers is shown in FIG. 4.

Figure 5A:
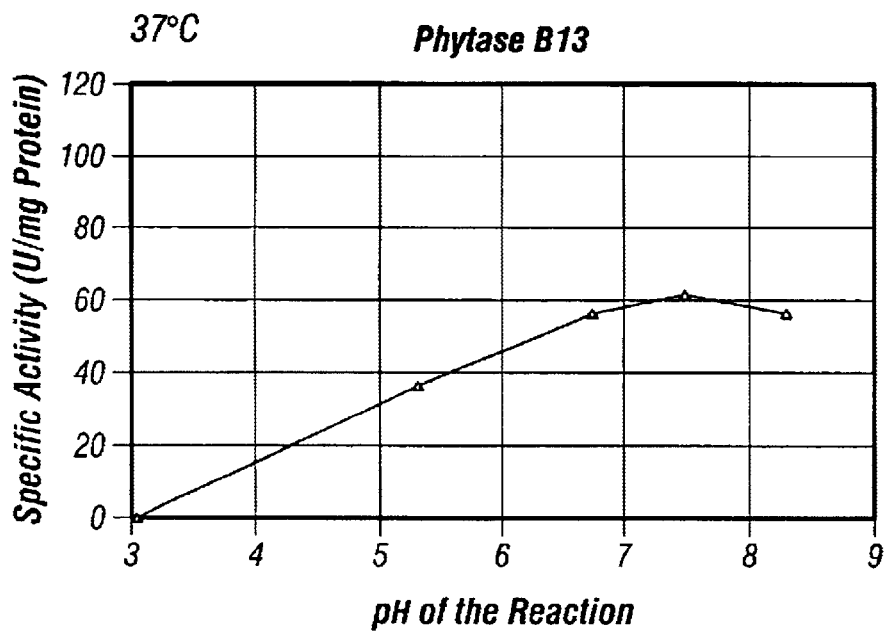
FIG. 5: Effect of pH on the activity of phytase in wheat bran extract at different temperatures.
Figure 5B:
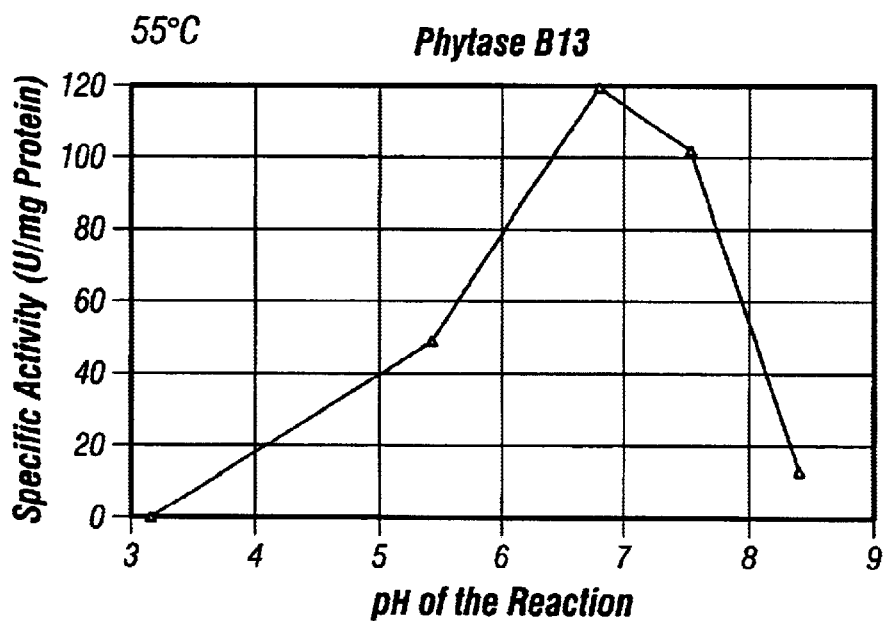
Figure 5C:
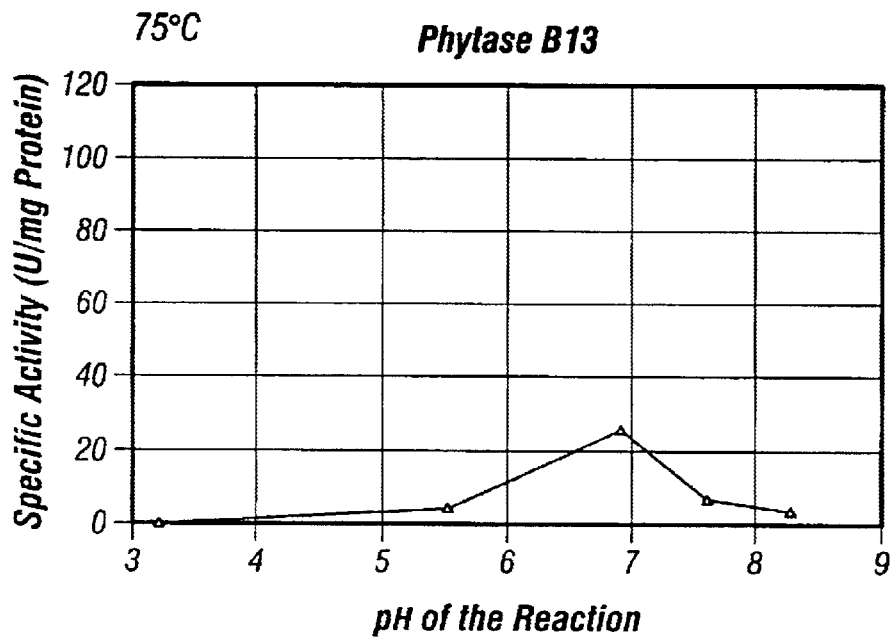
Figure 6:
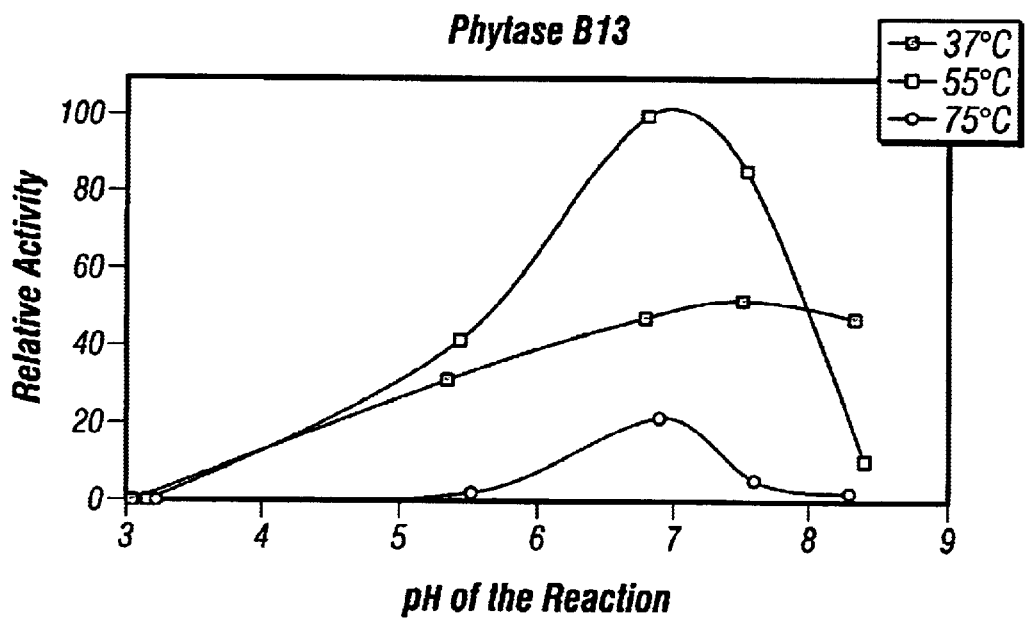
FIG. 6: Effect of pH on the temperature activity profile of phytase in wheat bran extract.

Wheat bran extract is likely to provide an environment that is closer to feed and animal digesta than any of the defined buffers. We determined the pH activity profiles of the phytases at 37, 55 and 75° C. Activity of the enzyme in wheat bran extract doubled as compared to its activity in defined buffers (FIGS. 5a to 5c). The profiles did not differ from those found in the defined buffers (FIG. 6).

Figure 7:
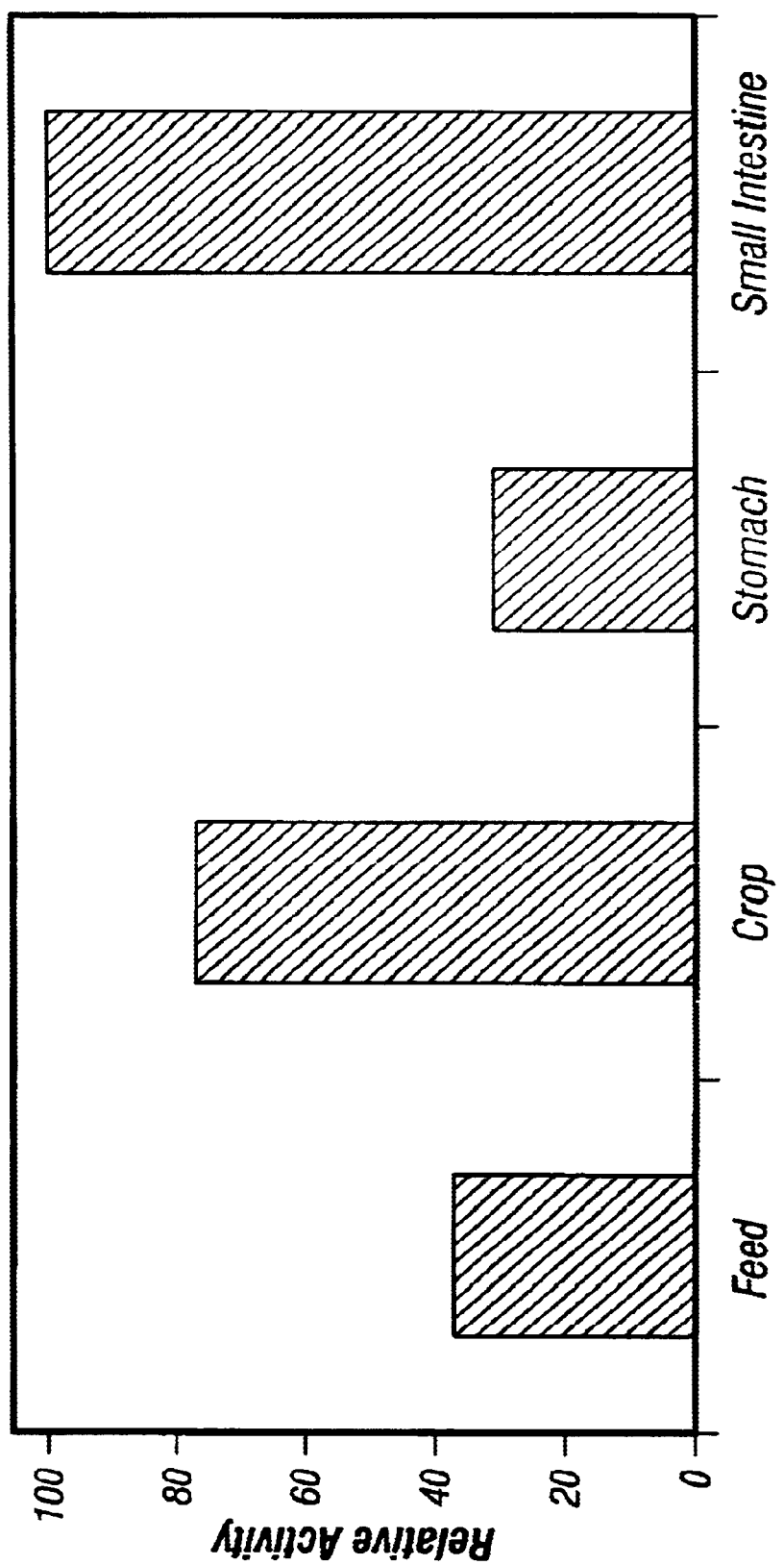
FIG. 7: Relative activity of phytase under pH and temperature corresponding to feed processing and digestion processes.

FIG. 7 illustrates the relative activity of the two phytases under pH and temperature conditions relevant to feed manufacturing and the digestive process of the broiler chicken. The data for this presentation has been taken from the experiment described above (FIGS. 5a to 5c).

EXAMPLE 2

Cloning of the Gene Encoding Phytase

N-Terminal Sequencing

The N-terminal sequence of B. subtilis B 13 phytase purified by SDS-PAGE was sequenced with a Perkin-Elmer Procice Sequencing System using Edman degradation. A twenty five amino acid long N-terminal sequence was obtained. To obtain more information about the amino acid sequence, the purified phytase was digested with lysC enzyme to obtain internal peptides and the digest was purified with RP-HPLC. LysC digestion was also performed to alcylated phytase following RP-HPLC purification. Non-alcylated RP-HPLC purified phytase peptides were sequenced with same system. Alcylation of phytase was done to determine whether possible sulphur bridges were present. There was no difference between alcylated and non-alcylated phytase lysC digestion RP-HPLC chromathograms showing that there were no sulphur bridges in the phytase.

Nineteen purified peptides were sequenced giving fourteen peptides which were different from each other (5 to 32 amino acids) and a total of 227 amino acids. All peptide sequences are shown in Table 4, including the sequence corresponding to the N-terminus of phytase. The molecular weight of the peptides was measured using mass spectrometer and compared with calculated molecular weights.

TABLE 4

Peptides obtained by N-terminal amino acid sequencing

| MW (det.) | MW (calc.) | amino acid sequence |
|---|---|---|
| | | LSDPYHFTVNAAAETEPVDTAGDAA * |
| | | LSDPYHFTVNAAAETEPVDTAGDAADDPAILD |
| 932 | 932.1 | YYAMVTGK |
| 1271.4 | 1271.3 | EGEFEQYELK |
| 1050.3 | 1050.2 | MLHSYNTGK |
| 798.9 | 798.9 | IVPWER |
| 2951.2 | 2948.4 | IVPWERIADQIGFRPLANEQVDPRK |
| 3467 | | NGTLQSMTDPDHPIATAINEVYGFTLWHSQ |
| 5450.2 | | YVADFRITDGPETDGTSDDDGII |
| 775.7 | 775.8 | LTDRSGK |
| 1317.9 | 1317.4 | VDIAAASNRSEGK |
| 2167.4 | 2167.4 | IADQIGFRPLANEQVDPRK |
| 720.7 | 720.8 | ANQNFK |

TABLE 4-continued

Peptides obtained by N-terminal amino acid sequencing

| MW (det.) | MW (calc.) | amino acid sequence |
|---|---|---|
| 619.6 | 619.7 | VRAFK |
| | | LNVVDIRYDFP |
| 1779.4 | 1778 | LNNVDIRYDFPLNGK |
| 1236.3 | 1236.4 | NTIEIYAIDGK |
| 1137.4 | 1137.3 | SGLVVYSLDGK |
| | | FSAEPDGGSNGTVIDRADGRHL |

* N-terminal sequence

Identification of Phytase Coding Sequences by PCR

On the basis of these peptide sequences, primers for PCR were designed (see Table 5). All PCR were performed using a PTC-255 DNA Engine and Perkin-Elmer Taq polymerase.

TABLE 5

PCR primers giving only one fragment each under optimal conditions

| number | oligonucleotide sequence |
|---|---|
| 6465 | TCIGATCCITATCATTTTACIGT |
| 6467 | AG(C/A)GGAAAATCATAIC(C/T) (G/A)ATATC |
| 6469 | CTTCIGAIC(G/T) (G/A)TTIGAIGCIGC |
| 6470 | TGATCIGC(G/A)ATIC(G/T)TTCCCA |
| 6471 | GC(G/A)AT(C/A)GGATGATC(C/A)GGATC |
| 6472 | TTCATA(C/T)TGTTCAAATTCICC |
| 6473 | TTICCIGT(G/A)TTATAIGAATGIA(G/A)CAT |
| 6474 | CCATC(G/A)ATIGCATA(G/A)ATTTC |
| 6541 | TTTAAA(G/A)TT(C/T)TG(G/A)TTIGC |
| 6544 | TTTICCIGTIACCATIGC |

Figure 8:
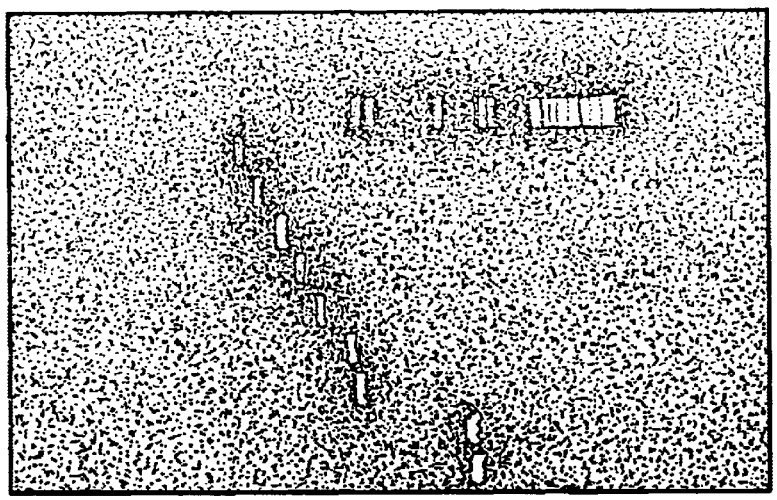
FIG. 8: Results of PCR amplification of gene encoding B. subtilis phytase using primers derived from amino acid sequence.

N = A, T, G or C;
I = inosine;

PCR was performed with these primers using *B. subtilis* B 13 DNA isolated according to Sambrook el al. (supra) as the template at different annealing temperatures (45, 50, 55 and 60 C) and at different magnesium concentrations (1.25, 2.5, 5 and 10 mM) to optimize PCR conditions. The following PCR portocool was chosen: 94° C. pre-melting for 2 min. before 30 cycles of 92° C. melting for 20 sec., 50° C. annealing for 30 sec., 72° C. extension for 60 sec. in 5 mM magnesium concertration. The primers given in Table 5 amplified only one fragment each under optimal conditions. These amplified PCR fragments are shown in FIG. 8.

The longest PCR fragment (amplified with primers 6465 and 6470) was cloned to pCR 2.1 vector (Invitrogen Corp., Inc., San Diego, USA) and sequenced using Sanger Dideoxy method. This resulted in determination of the partial DNA sequence (exact length 989 bp) of phytase of the present invention.

Restriction Enzyme Analysis of PCR Products of Phytase Gene

Figure 9:
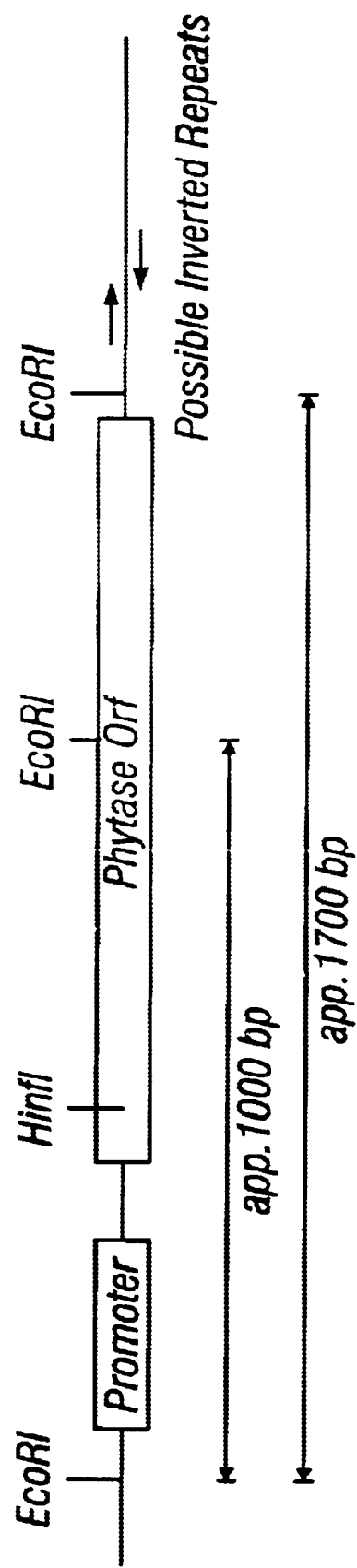
FIG. 9: Structure of B. subtilis phytase gene.

To verify that these PCR fragments were phytase fragments, restriction enzyme HinfI which cleaves the shortest PCR fragment into two approximately 100 bp long fragments was used. These fragments cut with HinfI gave the same sized fragment from the N-terminal end. PCR fragments were also cut with EcoRI; two of the longest phytase PCR fragments cut with EcoRI which confirms the scheme presented in the FIG. 9.

Southern Blot Analysis of Phytase of the Phytase Gene

Genomic DNA was isolated from *B. subtilis* B 13, as described in Sambrook et. al. (supra, 1989). Restriction enzymes used were those of Boehringer-Mannheim. *B. subtilis* B 13 DNA was partially digested with EcoRI and the fragments were separated on agarose gel. Separated fragments were Southern-Blotted to nylon membrane. Nylon membrane was Southern-Hybridized with 32P-labelled N-terminal oligonucleotide probe, GA(C/T)CC(G/A/T)TA(C/T)CA(C/T)TT(C/T)AC(G/A/T)GTNAA(C/T)GC (G/A/T)GC(G/A/T)GC(G/A/T)GAAAC, in order to determine the approximate size of the fragment containing the putative phytase gene. Southern-Hybridisation showed two bands of approximately 1700 bp and 1000 bp consistant with the structure of the gene given in FIG. 9.

Screening of a *B. subtilis* B 13 Genomic Library Partially EcoRI digested genomic *B. subtilis* B 13 DNA was cloned into Lambda ZapII using a Stratagene Lambda ZapII/EcoRI/CIAP Cloning kit according to the recommendations of the manufacturer. Lambda ZapII library was screened with Boehringer-Mannheim EasyToHyb hybridisation kit according the recommendations provided by the manufacturer using the above mentioned longest PCR fragment (989 bp) labeled with digoxigenin as the hybridisation probe.

XL-1 Blue MRF' host cells were infected with 100 000 pfu's of lambda ZapII *B. subtilis* B 13 genomic library phages. Infected cells were plated with TOP agarose on LB agar plates. Formed plaques were transferred to nylon membranes and screened with the 989 bp digoxigenin labeled hybridisation probe. Several intense positive clones were found with practically no backround. These positive plaques were cored and used in a second round of hybridisation. Positive plaques remained positive in a second round of hybridisation and were cored and excised with helper phage to obtain pBluescript SK(-) phagemid. Obtained phagemids were transformed to *E. coli* host cells and DNA from minipreps were used in analysis of insert DNA and DNA sequencing.

Determination of the DNA Sequence of the Gene Encoding Phytase

The DNA sequence encoding for phytase as well as the deduced amino acid sequence are shown in SEQ ID NO: 1. The molecular weight of phytase as deduced from the amino acid sequence in SEQ ID NO: 1 is ca. 41,900 daltons for the pre-protein and ca. 39,000 for the mature protein (i.e. without the signal sequence). This is in agreement with the molecular weight of phytase as determined from SDS-PAGE (FIG. 1).

The N-terminus of the mature protein corresponds to amino acid number 30 (Leu-30) of SEQ. ID. NO: 1.

EXAMPLE 3

Expression of Recombinant Phytase in *E. coli*

DNA coding for the mature protein was amplified by PCR using primers which also contained restriction sites for cloning into vectors pQE-30 and pQE-60 (Qiagen, Chatsworth, Cailf., USA) The 5' primer in each case encoded a MfeI site (compatible with EcoRI) followed by a ribosome binding site and the amino terminus of the mature protein. The 3' primer for the PQE-30 construct hybridized downstream of the stop codon of the native protein followed by a SalI site for cloning. The resulting PCR product was cloned into pQE-30 digested with EcoRI/SalI. This construct should produce the same protein as the mature native product with an additional methionine residue on the amino terminus.

5' primer for both pQE-30 and pQE-60 constructs:

```
GTTTCTCAATTGAAGGAGGAATTTAAATGCTGTCCGATCCTTATCATTTTAC
      Mfe I   RBS          MetLeuSerAspProTyrHisPhe
```

3' primer for pQE-30 construct:

```
       AATAAGTCGACGTACGACCGGATTCCGGCTGTGCT
            Sal I
```

The 3' primer used for the pQE-60 construct encoded the C-terminus of the protein (without stop codon) followed by a BglII cloning site. The vector sequence provides the nucleotides encoding a histidine tag to facilitate purification of the expressed protein. The PCR product was cloned into pQE-60 digested with EcoRI/BglII. The enzyme expressed from this construct can be purified from the cell lysate using Ni-NTA resin according to the manufacturer's instructions (Qiagen)

3' primer for pQE-60 construct:

```
       AATAAAGATCTTTTTCCGCTTCTGTCGGTCAGTT
            Bgl II
```

Said constructs were then transformed into the expression host M15/pREP4 cell line (Quiagen). The M15/pREP4 cell line was made competent and transformed using standard procedures (Sambrook, J., Fritsch, E. F. and Maniatis, T., Molecular Cloning, A Laboratory Manual, Cold Spring Harbor Press, Cold Spring Harbor, N.Y., 1989). This cell line contains a plasmid (pREP4) which constitutively expresses the lac repressor protein. This allows strong repression of the expression constructs in pQE-30 and pQE-60 which have two lac repressor recognition sequences upstream of the open reading frame. The vectors use the phage T5 promoter which is efficiently recognized by the *E. coli* RNA polymerase. These constructs were grown overnight in LB medium supplimented with ampicillin, methicillin and kanamycin at 37° C. The overnight cultures were diluted 1:30 in fresh media and grown to $OD_{600}$ 0.8 at which point they were induced with 1.5 mM IPTG. After three additional hours of growth, the cells were havested, washed, and lysed by sonication. The lysates were cleared of debris by centrifugation. Aliquots of cleared lysates were also assayed for enzyme activity. The assays were performed in reaction buffer (100 mM Tris-100 mM maleate, pH 7, 1 mM $CaCl_2$ and 2 mM sodium phytate) at 42° C. for 30 minutes. The results are presented in Table 6.

TABLE 6

| construct | assay | background | difference |
|---|---|---|---|
| pQE | 0.044 | 0.007 | 0.037 |
| pQE-30 | 0.259 | 0.002 | 0.257 |
| pQE-60 | 1.160 | 0.004 | 1.156 |

What is claimed is:

1. An isolated nucleic acid which encodes a phytase having a specific activity of at least about 20 U/mg protein and a pH optimum of at least 6.5, wherein said specific activity is determined by incubating said phytase in a solution containing about 100 mM Tris-HCl, at a pH of about 7.5, about 1 mM CaCl$_2$, and about 1.6 mM sodium phytate at about 37° C. for about 30 minutes, wherein the isolated nucleic acid hybridizes to SEQ. ID. No. 1 under standard conditions either in 6×SSC, 0.6% SDS, 50° C. overnight for Southern blotting or for PCR: 5 mM Mg$^{2++}$, Taq enzyme, premelting, 94° C. for 2 minutes and 30 cycles of melting at 92° C. for 20 seconds, annealing at 50° C. for 30 seconds and extension at 72° C. for 1 minute.

2. The isolated nucleic acid according to claim 1, wherein the nucleic acid is a DNA molecule.

3. A vector comprising:

an isolated DNA molecule which encodes a phytase having a specific activity of at least about 20 U/mg protein and a pH optimum of at least 6.5, wherein said specific activity is determined by incubating said phytase in a solution containing about 100 mM Tris-HCl, at a pH of about 7.5, about 1 mM CaCl$_2$, and about 1.6 mM sodium phytate at about 37° C. for about 30 minutes, wherein the isolated DNA molecule hybridizes to SEQ. ID. No. 1 under standard conditions either in 6×SSC, 0.5% SDS, 50° C. overnight for Southern blotting or for PCR: 5 mM Mg$^{2++}$, Taq enzyme, premelting, 94° C. for 2 minutes and 30 cycles of melting at 92° C. for 20 seconds, annealing at 50° C. for 30 seconds and extension at 72° C. for 1 minute, wherein the DNA molecule is functionally linked to regulatory sequences capable of expressing a phytase from said DNA sequence.

4. The vector according to claim 3 wherein the, DNA molecule further comprises a leader sequence capable of providing for the secretion of said phytase.

5. A prokaryotic host cell transformed by a nucleic acid, wherein the nucleic acid is an isolated nucleic acid which encodes a phytase having a specific activity of at least about 20 U/mg protein and a pH optimum of at least 6.5, wherein said specific activity is determined by incubating said phytase in a solution containing about 100 mM Tris-HCl, at a pH of about 7.5, about 1 mM CaCl$_2$, and about 1.6 mM sodium phytate at about 37° C. for about 30 minutes, wherein the isolated nucleic acid hybridizes to SEQ. ID. No. 1 under standard conditions either in 6×SSC, 0.6% SDS, 50° C. overnight for Southern blotting or for PCR: 5 mM Mg$^{2++}$, Taq enzyme, premelting, 94° C. for 2 minutes and 30 cycles of melting at 92° C. for 20 seconds, annealing at 50° C. for 30 seconds and extension at 72° C. for 1 minute.

6. A prokaryotic host cell according to claim 5, wherein the host cell is selected from the group comprising *E. coli*, Bacillus sp., Lactobacillus sp. and Lactococcus sp.

7. A eukaryotic host cell or organism transformed by a nucleic acid, wherein the nucleic acid is an isolated nucleic acid which encodes a phytase having a specific activity of at least about 20 U/mg protein and a pH optimum of at least 6.5, wherein said specific activity is determined by incubating said phytase in a solution containing about 100 mM Tris-HCl, at a pH of about 7.5, about 1 mM CaCl$_2$, and about 1.6 mM sodium phytate at about 37° C. for about 30 minutes, wherein the isolated nucleic acid hybridizes to SEQ. ID. No. 1 under standard conditions either in 6×SSC, 0.6% SDS, 50° C. overnight for Southern blotting or for PCR: 5 mM Mg$^{2++}$, Taq enzyme, premelting, 94° C. for 2 minutes and 30 cycles of melting at 92° C. for 20 seconds, annealing at 50° C. for 30 seconds and extension at 72° C. for 1 minute.

8. A eukaryotic host cell or organism according to claim 7, wherein the host cell is selected from the group comprising Aspergillus sp., Humicola sp., Pichia sp., Trichoderma sp. Saccharomyces sp. and plants such as soybean, corn and rapeseed.

9. A method for the production of phytase comprising:

transforming a prokaryotic host cell with an isolated nucleic acid, wherein the isolated nucleic acid encodes a phytase having a specific activity of at least about 20 U/mg protein and a pH optimum of at least 6.5, wherein said specific activity is determined by incubating said phytase in a solution containing about 100 mM Tris-HCl, at a pH of about 7.5, about 1 mM CaCl$_2$, and about 1.6 mM sodium phytate at about 37° C. for about 30 minutes, wherein the isolated nucleic acid hybridizes to SEQ. ID. No. 1 under standard conditions either in 6×SSC, 0.6% SDS, 50° C. overnight for Southern blotting or for PCR: 5 mM Mg$^{2++}$, Taq enzyme, premelting, 94° C. for 2 minutes and 30 cycles of melting at 92° C. for 20 seconds, annealing at 50° C. for 30 seconds and extension at 72° C. for 1 minute;

culturing or cultivating the prokaryotic host cell under conditions effective for producing phytase; and recovering phytase.

10. A method for the production of a nucleic acid which encodes a phytase, wherein a probe comprising a nucleic acid which encodes a phytase is hybridized to a sample suspected of containing said nucleic, under standard hybridization conditions either in 6×SSC, 0.6% SDS, 50° C. overnight or functional equivalents thereof for Southern blotting or for PCR 5 mM Mg$^{2++}$, Taq enzyme, premelting, 94° C. for 2 minutes and 30 cycles of metlting at 92° C. for 20 seconds, annealing at 50° C. for 30 seconds and extensioin at 72° C. for 1 minute, wherein the nucleic acid which encodes a phytase has a specific activity of at least about 20 U/mg protein and a pH optimum of at least 6.5, wherein said specific activity is determined by incubating said phytase in a solution containing about 100 mM Tris-HCl, at a pH of about 7.5, about 1 mM CaCl$_2$, and about 1.6 mM sodium phytate at about 37° C. for about 30 minutes, wherein the isolated nucleic acid hybridizes to SEQ. ID. No. 1 under standard conditions either in 6×SSC, 0.6% SDS, 50° C. overnight for Southern blotting or for PCR: 5 mM Mg$^{2++}$, Taq enzyme, premelting, 94° C. for 2 minutes and 30 cycles of melting at 92° C. for 20 seconds, annealing at 50° C. for 30 seconds and extension at 72° C. for 1 minute.

11. A method for the production of phytase comprising:

transforming a eukaryotic host cell with an isolated nucleic acid, wherein the isolated nucleic acid encodes a phytase having a specific activity of at least about 20 U/mg protein and a pH optimum of at least 6.5, wherein said specific activity is determined by incubating said phytase in a solution containing about 100 mM Tris-HCl, at a pH of about 7.5, about 1 mM $CaCl_2$, and about 1.6 mM sodium phytate at about 37° C. for about 30 minutes, wherein the isolated nucleic acid hybridizes to SEQ. ID. No. 1 under standard conditions either in 6×SSC, 0.6% SDS, 50° C. overnight for Southern blotting or for PCR: 5 mM $Mg^{2++}$, Taq enzyme, premelting, 94° C. for 2 minutes and 30 cycles of melting at 92° C. for 20 seconds, annealing at 50° C. for 30 seconds and extension at 72° C. for 1 minute;

culturing or cultivating the eukaryotic host cell under conditions effective for producing phytase; and recovering phytase.

* * * * *

SEQUENCE LISTING

<160> NUMBER OF SEQ ID NOS: 2

<210> SEQ ID NO 1
<211> LENGTH: 1290
<212> TYPE: DNA
<213> ORGANISM: Bacillus subtilis
<220> FEATURE:
<221> NAME/KEY: CDS
<222> LOCATION: (91)...(1239)

<400> SEQUENCE: 1

```
cacatttgac aattttcaca aaacttaac actgacaatc atgtatatat gttacaattg      60
aagtgcacgt tcataaaagg aggaagtaaa atg aat cat tca aaa aca ctt ttg     114
                                 Met Asn His Ser Lys Thr Leu Leu
                                  1               5 tta acc gcg gcg gcc gga ctg atg ctc aca tgc ggt gcg gtg tct tcc     162
Leu Thr Ala Ala Ala Gly Leu Met Leu Thr Cys Gly Ala Val Ser Ser
         10                  15                  20 cag gca aag cat aag ctg tcc gat cct tat cat ttt acc gtg aat gca     210
Gln Ala Lys His Lys Leu Ser Asp Pro Tyr His Phe Thr Val Asn Ala
 25                  30                  35                  40 gcg gcg gaa acg gaa ccg gtt gat acg gcc ggt gac gcg gct gat gat     258
Ala Ala Glu Thr Glu Pro Val Asp Thr Ala Gly Asp Ala Ala Asp Asp
                 45                  50                  55 cct gcg att tgg ctg gac ccc aag act cct cag aac agc aaa ttg att     306
Pro Ala Ile Trp Leu Asp Pro Lys Thr Pro Gln Asn Ser Lys Leu Ile
             60                  65                  70 acg acc aat aaa aaa tca ggt tta gtc gtt tac agc ctt gat ggt aag     354
Thr Thr Asn Lys Lys Ser Gly Leu Val Val Tyr Ser Leu Asp Gly Lys
```

```
                75                  80                  85
atg ctt cat tcc tat aat acc ggg aag ctg aac aat gtc gat atc cgt     402
Met Leu His Ser Tyr Asn Thr Gly Lys Leu Asn Asn Val Asp Ile Arg
         90                  95                 100 tat gat ttt ccg ttg aac ggc aaa aaa gtc gat atc gcg gca gca tcc     450
Tyr Asp Phe Pro Leu Asn Gly Lys Lys Val Asp Ile Ala Ala Ala Ser
105                 110                 115                 120 aat cgg tct gaa gga aaa aat acc att gag att tac gct att gat gga     498
Asn Arg Ser Glu Gly Lys Asn Thr Ile Glu Ile Tyr Ala Ile Asp Gly
                125                 130                 135 aaa aac ggc aca tta caa agc atg aca gat cca gac cat ccg att gca     546
Lys Asn Gly Thr Leu Gln Ser Met Thr Asp Pro Asp His Pro Ile Ala
                140                 145                 150 aca gca att aat gag gta tac ggt ttt acc tta tac cac agt caa aaa     594
Thr Ala Ile Asn Glu Val Tyr Gly Phe Thr Leu Tyr His Ser Gln Lys
            155                 160                 165 aca gga aaa tat tac gcg atg gtg aca gga aaa gag ggt gaa ttt gaa     642
Thr Gly Lys Tyr Tyr Ala Met Val Thr Gly Lys Glu Gly Glu Phe Glu
170                 175                 180 caa tac gaa tta aag gcg gac aaa aat gga tac ata tcc ggc aaa aag     690
Gln Tyr Glu Leu Lys Ala Asp Lys Asn Gly Tyr Ile Ser Gly Lys Lys
185                 190                 195                 200 gta cgg gcg ttt aaa atg aat tcc cag acg gaa ggg atg gca gca gac     738
Val Arg Ala Phe Lys Met Asn Ser Gln Thr Glu Gly Met Ala Ala Asp
                205                 210                 215 gat gaa tac ggc agg ctt tat atc gca gaa gaa gat gag gcc att tgg     786
Asp Glu Tyr Gly Arg Leu Tyr Ile Ala Glu Glu Asp Glu Ala Ile Trp
        220                 225                 230 aag ttc agc gcc gag ccg gac ggc ggc agt aac gga acg gtt atc gac     834
Lys Phe Ser Ala Glu Pro Asp Gly Gly Ser Asn Gly Thr Val Ile Asp
        235                 240                 245 cgt gcc gac ggc agg cat tta act cgt gat att gaa gga ttg acg att     882
Arg Ala Asp Gly Arg His Leu Thr Arg Asp Ile Glu Gly Leu Thr Ile
        250                 255                 260 tac tac gct gct gac ggg aaa ggc tat ctg atg gca tca agc cag gga     930
Tyr Tyr Ala Ala Asp Gly Lys Gly Tyr Leu Met Ala Ser Ser Gln Gly
265                 270                 275                 280 aac agc agc tac gcc att tat gac aga caa gga aag aac aaa tat gtt     978
Asn Ser Ser Tyr Ala Ile Tyr Asp Arg Gln Gly Lys Asn Lys Tyr Val
                285                 290                 295 gcg gat ttt cgc ata aca gac ggt cct gaa aca gac ggg aca agc gat    1026
Ala Asp Phe Arg Ile Thr Asp Gly Pro Glu Thr Asp Gly Thr Ser Asp
            300                 305                 310 aca gac gga att gac gtt ctg ggt ttc gga ctg ggg cct gaa tat ccg    1074
Thr Asp Gly Ile Asp Val Leu Gly Phe Gly Leu Gly Pro Glu Tyr Pro
            315                 320                 325 ttc ggt att ttt gtc gca cag gac ggt gaa aat ata gat cac ggc caa    1122
Phe Gly Ile Phe Val Ala Gln Asp Gly Glu Asn Ile Asp His Gly Gln
        330                 335                 340 aag gcc aat caa aat ttt aaa atc gtg cca tgg gaa aga att gct gat    1170
Lys Ala Asn Gln Asn Phe Lys Ile Val Pro Trp Glu Arg Ile Ala Asp
345                 350                 355                 360 caa atc ggt ttc cgc ccg ctg gca aat gaa cag gtt gac ccg aga aaa    1218
Gln Ile Gly Phe Arg Pro Leu Ala Asn Glu Gln Val Asp Pro Arg Lys
                365                 370                 375 ctg acc gac aga agc gga aaa taaacatgca aaaagcagct tatacaagct       1269
Leu Thr Asp Arg Ser Gly Lys
                380 gcttttttgca tgtgaagaac g                                           1290
```

```
<210> SEQ ID NO 2
<211> LENGTH: 383
<212> TYPE: PRT
<213> ORGANISM: Bacillus subtilis

<400> SEQUENCE: 2

Met Asn His Ser Lys Thr Leu Leu Thr Ala Ala Gly Leu Met
  1               5                  10                  15

Leu Thr Cys Gly Ala Val Ser Ser Gln Ala Lys His Lys Leu Ser Asp
                 20                  25                  30

Pro Tyr His Phe Thr Val Asn Ala Ala Glu Thr Glu Pro Val Asp
             35                  40                  45

Thr Ala Gly Asp Ala Ala Asp Asp Pro Ala Ile Trp Leu Asp Pro Lys
         50                  55                  60

Thr Pro Gln Asn Ser Lys Leu Ile Thr Thr Asn Lys Lys Ser Gly Leu
 65                  70                  75                  80

Val Val Tyr Ser Leu Asp Gly Lys Met Leu His Ser Tyr Asn Thr Gly
                 85                  90                  95

Lys Leu Asn Asn Val Asp Ile Arg Tyr Asp Phe Pro Leu Asn Gly Lys
             100                 105                 110

Lys Val Asp Ile Ala Ala Ala Ser Asn Arg Ser Glu Gly Lys Asn Thr
         115                 120                 125

Ile Glu Ile Tyr Ala Ile Asp Gly Lys Asn Gly Thr Leu Gln Ser Met
130                 135                 140

Thr Asp Pro Asp His Pro Ile Ala Thr Ala Ile Asn Glu Val Tyr Gly
145                 150                 155                 160

Phe Thr Leu Tyr His Ser Gln Lys Thr Gly Lys Tyr Tyr Ala Met Val
                 165                 170                 175

Thr Gly Lys Glu Gly Glu Phe Glu Gln Tyr Glu Leu Lys Ala Asp Lys
             180                 185                 190

Asn Gly Tyr Ile Ser Gly Lys Lys Val Arg Ala Phe Lys Met Asn Ser
         195                 200                 205

Gln Thr Glu Gly Met Ala Ala Asp Asp Glu Tyr Gly Arg Leu Tyr Ile
210                 215                 220

Ala Glu Glu Asp Glu Ala Ile Trp Lys Phe Ser Ala Glu Pro Asp Gly
225                 230                 235                 240

Gly Ser Asn Gly Thr Val Ile Asp Arg Ala Asp Gly Arg His Leu Thr
                 245                 250                 255

Arg Asp Ile Glu Gly Leu Thr Ile Tyr Tyr Ala Ala Asp Gly Lys Gly
             260                 265                 270

Tyr Leu Met Ala Ser Ser Gln Gly Asn Ser Ser Tyr Ala Ile Tyr Asp
         275                 280                 285

Arg Gln Gly Lys Asn Lys Tyr Val Ala Asp Phe Arg Ile Thr Asp Gly
290                 295                 300

Pro Glu Thr Asp Gly Thr Ser Asp Thr Asp Gly Ile Asp Val Leu Gly
305                 310                 315                 320

Phe Gly Leu Gly Pro Glu Tyr Pro Phe Gly Ile Phe Val Ala Gln Asp
                 325                 330                 335

Gly Glu Asn Ile Asp His Gly Gln Lys Ala Asn Gln Asn Phe Lys Ile
             340                 345                 350

Val Pro Trp Glu Arg Ile Ala Asp Gln Ile Gly Phe Arg Pro Leu Ala
         355                 360                 365

Asn Glu Gln Val Asp Pro Arg Lys Leu Thr Asp Arg Ser Gly Lys
```